US008251949B2

(12) United States Patent
Warnack

(10) Patent No.: US 8,251,949 B2

(45) Date of Patent: Aug. 28, 2012

(54) BALLOON CATHETER WITH RADIOPAQUE MARKER

(75) Inventor: Boris Warnack, Neuhausen (CH)

(73) Assignee: Abbott Laboratories, Abbott Park, IL (US)

(*) Notice: Subject to any disclaimer, the term of this patent is extended or adjusted under 35 U.S.C. 154(b) by 951 days.

(21) Appl. No.: 11/775,480

(22) Filed: Jul. 10, 2007

(65) Prior Publication Data

US 2008/0015499 A1 Jan. 17, 2008

Related U.S. Application Data

(63) Continuation-in-part of application No. 10/523,897, filed as application No. PCT/EP03/08493 on Jul. 31, 2003, now Pat. No. 7,322,959.

(30) Foreign Application Priority Data

Aug. 6, 2002 (EP) .................................... 02017547

(51) Int. Cl.
*A61M 31/00* (2006.01)
*A61M 37/00* (2006.01)
*A61B 18/18* (2006.01)

(52) U.S. Cl. ......... 604/103.01; 604/103.03; 604/103.06; 606/41

(58) Field of Classification Search .................. 606/108, 606/41; 604/103.01–103.09, 500
See application file for complete search history.

(56) References Cited

U.S. PATENT DOCUMENTS 4,571,240 A 2/1986 Samson et al.
4,938,220 A 7/1990 Mueller, Jr.
5,484,409 A 1/1996 Atkinson et al.
5,485,667 A * 1/1996 Kleshinski ...................... 29/447
5,545,135 A 8/1996 Iacob et al.
5,547,472 A * 8/1996 Onishi et al. ............. 604/103.01
5,666,969 A * 9/1997 Urick et al. ................... 600/585
5,741,327 A 4/1998 Frantzen
5,799,731 A 9/1998 Avakov et al.
6,022,374 A 2/2000 Imran (Continued)

FOREIGN PATENT DOCUMENTS

EP 0597506 5/1994

(Continued)

OTHER PUBLICATIONS

U.S. Appl. No. 10/523,897, (US 7,322,959), filed Sep. 19, 2005 (Jan. 29, 2008).

(Continued)

*Primary Examiner* — Nicholas Lucchesi
*Assistant Examiner* — Ian Holloway
(74) *Attorney, Agent, or Firm* — Baker Botts LLP

(57) ABSTRACT

A catheter for delivering a stent includes an outer tube having a proximal end, a distal end and a wall defining a lumen; an inner tube disposed within the outer tube and defining a lumen for a guidewire, wherein a portion of a length of the inner tube is wrapped around with a spiral-shaped wire; a balloon sealingly connected to the inner tube and the outer tube adjacent the distal ends thereof, the balloon defining an interior volume and having an exterior surface; and a marker made from a wire of a highly radiopaque and ductile material, wherein the wire is wrapped in a plurality of at least partially overlapping layers such that the marker is flexible along the length of the catheter.

49 Claims, 4 Drawing Sheets

U.S. PATENT DOCUMENTS

| | | | | |
|---|---|---|---|---|
| 6,123,703 | A * | 9/2000 | Tu et al. | 606/41 |
| 6,129,708 | A | 10/2000 | Enger | |
| 6,371,961 | B1 * | 4/2002 | Osborne et al. | 606/108 |
| 6,375,774 | B1 | 4/2002 | Lunn et al. | |
| 6,464,720 | B2 | 10/2002 | Boatman et al. | |
| 6,488,653 | B1 * | 12/2002 | Lombardo | 604/103.06 |
| 6,500,147 | B2 | 12/2002 | Omaleki et al. | |
| 6,503,271 | B2 | 1/2003 | Duerig et al. | |
| 6,520,934 | B1 | 2/2003 | Lee et al. | |
| 6,540,721 | B1 | 4/2003 | Voyles et al. | |
| 6,761,708 | B1 | 7/2004 | Chiu et al. | |
| 2002/0007146 | A1 | 1/2002 | Omaleki et al. | |
| 2002/0038103 | A1 * | 3/2002 | Estrada et al. | 604/103.09 |
| 2003/0105426 | A1 | 6/2003 | Jorgensen | |
| 2003/0144725 | A1 | 7/2003 | Lombardi | |
| 2003/0176837 | A1 | 9/2003 | Fitzmaurice et al. | |
| 2004/0015229 | A1 | 1/2004 | Fulkerson et al. | |
| 2005/0060025 | A1 | 3/2005 | Mackiewicz et al. | |
| 2006/0024174 | A1 | 2/2006 | Welch | |

FOREIGN PATENT DOCUMENTS

| | | |
|---|---|---|
| EP | 0855171 | 7/1998 |
| WO | WO93/20883 | 10/1993 |
| WO | WO98/07390 | 2/1998 |

OTHER PUBLICATIONS

U.S. Appl. No. 10/523,897, Nov. 26, 2007 Issue Fee Payment.

U.S. Appl. No. 10/523,897, Aug. 24, 2007 Notice of Allowance.

U.S. Appl. No. 10/523,897, Aug. 8, 2007 Response to Final Office Action.

U.S. Appl. No. 10/523,897, Apr. 18, 2007 Final Office Action.

U.S. Appl. No. 10/523,897, Jan. 22, 2007 Response to Non-Final Office Action.

U.S. Appl. No. 10/523,897, Oct. 16, 2006 Non-Final Office Action.

* cited by examiner

BALLOON CATHETER WITH RADIOPAQUE MARKER

CROSS REFERENCE TO RELATED APPLICATIONS

This application is a continuation-in-part application of U.S. patent application Ser. No. 10/523,897 filed Sep. 19, 2005, now U.S. Pat. No. 7,322,959, which is a National stage of PCT/EP03/08493, filed Jul. 31, 2003, and which claims priority to EP 02017547.7, filed Aug. 6, 2002, the contents of each of which are incorporated herein by reference.

BACKGROUND OF THE INVENTION

1. Field of the Invention

The invention relates to a catheter having a shaft body that incorporates a spiral-shaped radiopaque wire to improve the visibility of the shaft and kink-resistance and push transfer capability of the catheter. Particularly, the invention relates to a catheter for use in delivering a stent which has a radiopaque shaft and exhibits kink resistance.

2. Description of Related Art

Cardiovascular disease is prevalent in the United States and in other parts of the world. One manifestation of cardiovascular disease is atherosclerosis, which is the buildup of plaque (or fatty deposits) on the walls of blood vessels, such as coronary arteries. This buildup of plaque can grow large enough to reduce blood flow through the blood vessel. Serious damage results when an area of plaque ruptures and forms a clot, which travels to another part of the body. If the blood vessels that feed the heart are blocked, a heart attack results. If the blood vessels to the brain are blocked, a stroke results. Thus, atherosclerosis can be fatal for some people.

Typically, physicians treat atherosclerosis by implanting a tubular endoprosthesis such as a stent at the narrowed or blocked segment of the blood vessel, which widens and holds open the blood vessel. To perform this procedure the stent is delivered to the site of the lesion in the blood vessel by a catheter assembly, otherwise known as a stent delivery device. The stent delivery device enters the vasculature of the patient through the femoral artery and travels through a tortuous path to the site of the lesion. The physician positions the stent across the lesion and deploys the stent so that the stent forces the plaque against the inside wall of the blood vessel (or lumen) and maintains its expanded configuration so that the patency of the blood vessel is maintained.

A previously proposed catheter, for use in delivering a stent, is described in WO 98/07390, for example. The known catheter in the form of a stent delivery system comprises short solid marker bands made from a radiopaque material. These marker bands constitute solid tubes. The drawback of these tubes is the increase of profile of the balloon and, even more important, the resulting rigid length of between 1 mm to 1.2 mm which, in turn, results in a reduction in flexibility of the catheter tube. Therefore, the known catheter, when pushed forward through a curved vessel, suffers from the drawback of an undesired stiffness in the region of the marker bands diminishing especially the trackability of the catheter. Finally, this stiffening of the catheter tube results in a certain danger of buckling of the catheter.

Thus, for the aforementioned reasons, there is a need for a catheter having an improved resistance to buckling and an improved push transfer capability and greater visibility.

SUMMARY OF THE INVENTION

The invention provides a catheter, in particular for use in delivering a stent, that overcomes the aforementioned drawbacks of previously proposed catheters and provides a marker arrangement that exhibits improved visualization under fluoroscopic equipment along with a sufficient flexibility and trackability of the catheter. In particular, the invention provides a catheter comprising an elongate first tubular member having a proximal section, a distal section, and a lumen extending therethrough and a balloon associated with the distal section of the first tubular member. A wire is disposed along at least the distal section of the first tubular member in a spiral configuration. The wire includes at least a section of radiopaque material, thereby defining a marker section. For example and not limitation, the wire can have a circular cross-section or a flat rectangular cross-section.

In an embodiment, the radiopaque material is disposed along the elongate tubular member such that it is disposed between the proximal and distal ends of the balloon. If desired, the wire can further include a second marker section of radiopaque material. In this manner, for example, the first marker section can disposed proximate the proximal end of the balloon and the second marker section can be disposed proximate the distal end of the balloon. Further, if desired, the first marker section of radiopaque material can be configured to extend along the tubular member such that the marker extends from the proximal end to the distal end of the balloon.

To achieve desired flexibility and kink resistance, the wire can include a plurality of densities along the length of the tubular member. Additionally, the wire can be configured to include a spiral having a plurality of pitches along the length of the tubular member. For example, the wire can include a first spiral configuration having a first pitch proximal to the proximal end of the balloon and a second spiral configuration having a second pitch distal to the proximal end of the balloon. The first and second pitches could be varied. In this manner, a plurality of pitches can define a stiffness gradient along the length of the tubular member. For example, the stiffness gradient decreases distally along the length of the tubular member. If desired, however, the stiffness gradient can increase distally along the length of the tubular member. Alternatively, varying stiffness can be achieved along the tubular member, if desired.

In an embodiment, the wire is embedded into the outer surface of the tubular member. However, other methods for incorporating the wire to the tubular member is feasible. For instance, the wire can be adhered to the surface of the tubular member, if desired. The catheter can further include a cover disposed over the wire. The cover can be a coating over the wire or a tubular member disposed on the exposed surface of the wire.

One feature of the catheter according to an embodiment of the invention includes an outer tube having a proximal end, a distal end and a wall defining a lumen; an inner tube disposed within the outer tube and defining a lumen for a guidewire, wherein a portion of a length of the inner tube is wrapped around with a spiral-shaped wire; a balloon sealingly connected to the inner tube and the outer tube adjacent the distal ends thereof, the balloon defining an interior volume and having an exterior surface; and a marker made from a wire of a highly radiopaque and ductile material, wherein the wire is wrapped in a plurality of at least partially overlapping layers such that the marker is flexible along the length of the catheter.

The provision of markers being made of a wire of a highly radiopaque and ductile material reduces the rigid length of the markers as the wire provides higher flexibility and also less profile. Therefore, the catheter according to an embodiment of the invention provides a high flexibility and trackability and, simultaneously, the indication of the length of the cylindrical part of the balloon or the length of a stent mounted on the balloon is ensured by the highly radiopaque and ductile material of the wire-markers.

An embodiment of the catheter according to an embodiment of the invention provides for a wire that is wrapped around the inner tube and preferably at least partly embedded in the tube material. Furthermore, it is possible to build up different kinds of wire arrangements, especially the wire arrangement of a plurality of at least partly overlapping layers that further enhances the radiopacity.

Preferred diameters of the wire according to an embodiment of the invention are 0.01, 0.02 and/or 0.04 mm. The free ends of the wire can be fixed either mechanically or by using an adhesive bonding.

BRIEF DESCRIPTION OF THE DRAWINGS

The following is a description of some specific embodiments of the invention, reference being made to the accompanying drawings, in which

FIG. 5 is a schematically simplified view of the reaction of a marker according to an embodiment of the invention upon bending of the catheter tube the marker band is mounted on;

DETAILED DESCRIPTION OF EMBODIMENTS OF THE INVENTION

While this invention may be embodied in many different forms, reference will now be made in detail to specific embodiments of the invention. This description is an exemplification of the principles of the invention and is not intended to limit the invention to the particular embodiments illustrated. For the purposes of this disclosure, like reference numbers in the figures shall refer to like features unless otherwise indicated.

It will be apparent to those skilled in the art that various modifications and variations can be made to the catheter without departing from the spirit or scope of the invention. Thus, it is intended that the present invention include modifications and variations that are within the scope of the appended claims and their equivalents.

Figure 1:
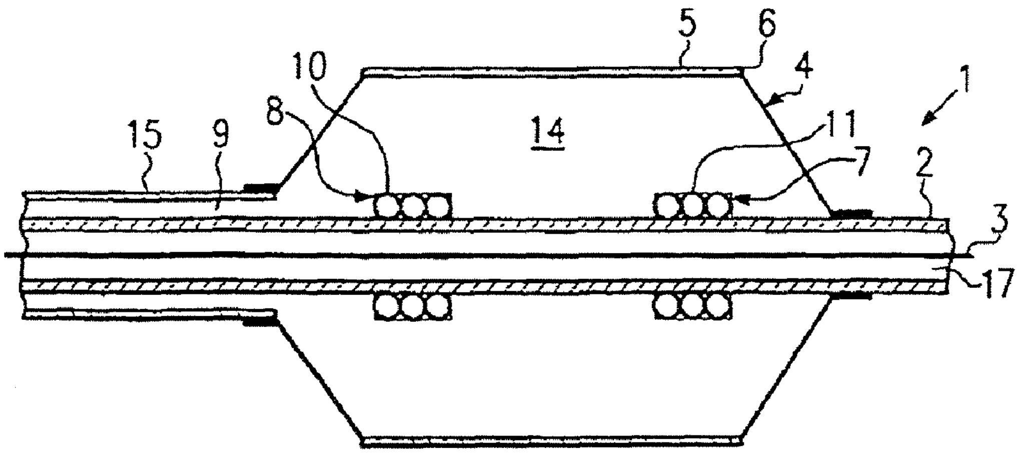
FIG. 1 is a schematically simplified view of the distal end of a catheter according to an embodiment of the invention.

FIG. 1 depicts a catheter 1 that is particularly adapted for use in delivering a stent 5 disposed on an exterior surface 6 of a balloon 4 of the catheter 1. In accordance with an embodiment of the invention, balloon 4 is sealingly connected to a first outer tube 15 adjacent to the distal end of the balloon. The balloon 4 defines an interior volume 14 that is in communication with a first lumen 9 of the first outer tube 15. So, e.g., a heated fluid can be introduced through the proximal end of the first lumen 9 in order to pressurize the balloon 4 and to heat the stent engagement region 6.

FIG. 1, furthermore, displays a second inner tube 2 that, for the depicted embodiment, is disposed concentrically within the first outer tube 15. This second inner tube 2 defines a second inner lumen 17 for a guidewire 3.

Finally, the catheter 1 includes a marker arrangement 7, 8 that is disposed on the second inner tube 3 within interior volume 14 of balloon 4.

The preferred embodiment of the catheter shown in FIG. 1 includes two markers 10, 11, constituting the marker arrangement 7, 8 and being made from a wire of a highly radiopaque and ductile material.

Figure 2:
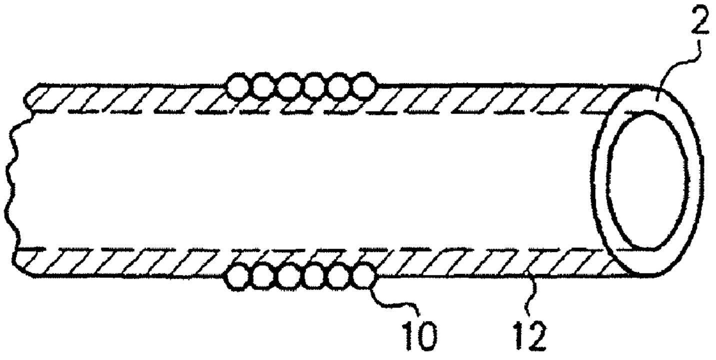
FIGS. 2 to 4 are different marker arrangements according to embodiments of the invention.

FIG. 2 shows a part of the second inner tube 2 with the marker 10 being partly embedded within the wall material 12 of tube 2. In another embodiment of the invention, the wire of marker 10 can also be totally embedded in material 12 of the wall of the second inner tube 2.

Figure 3:
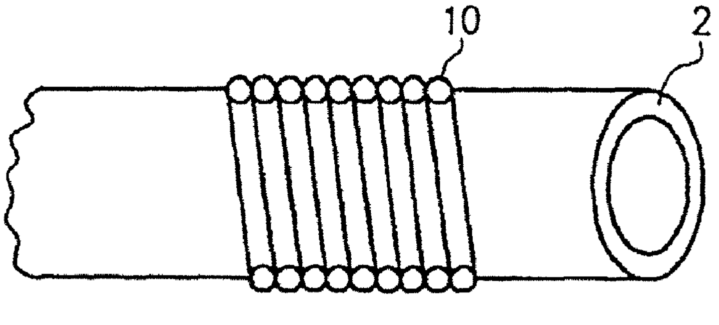

FIG. 3 depicts also a part of second inner tube 2 showing a coil-like marker 10 that can also be embedded partly or totally within the material 12 of the tube wall.

Figure 4:
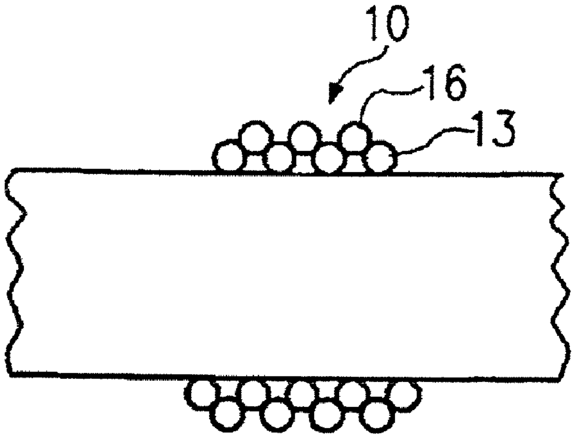

FIG. 4 shows a particularly advantageous embodiment of the marker 10 (or, of course, also of marker 11) comprising two layers 13, 16 of partly overlapping wires.

Figure 5:
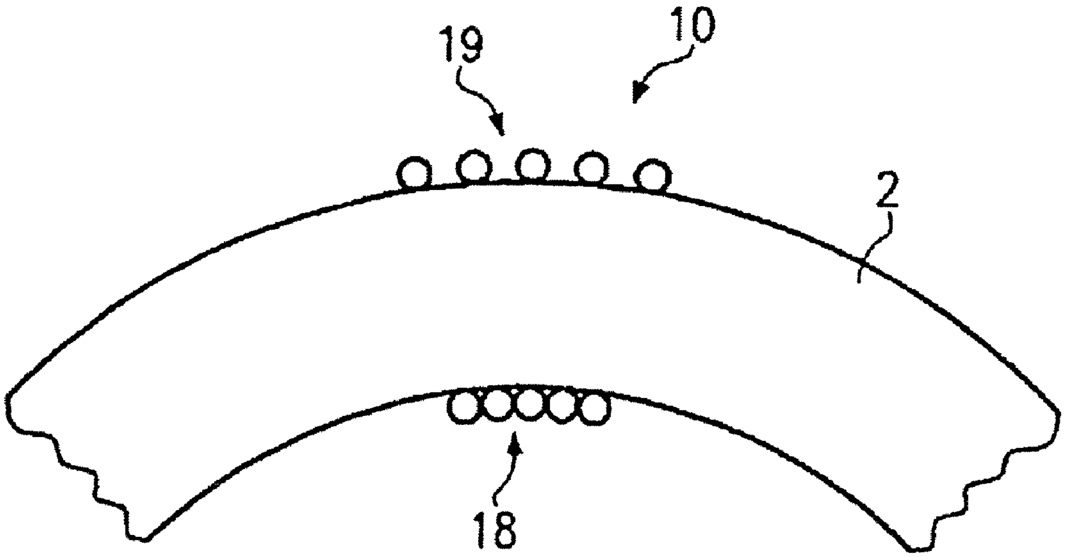

FIG. 5 depicts tube 2 in a bent state. The inner part 18 of the wire marker 10 or 11 is compressed in this state while the outer part 19 of marker 10 is expanded thus ensuring a higher flexibility and trackability of the catheter 1 according to the present invention.

Figure 7:
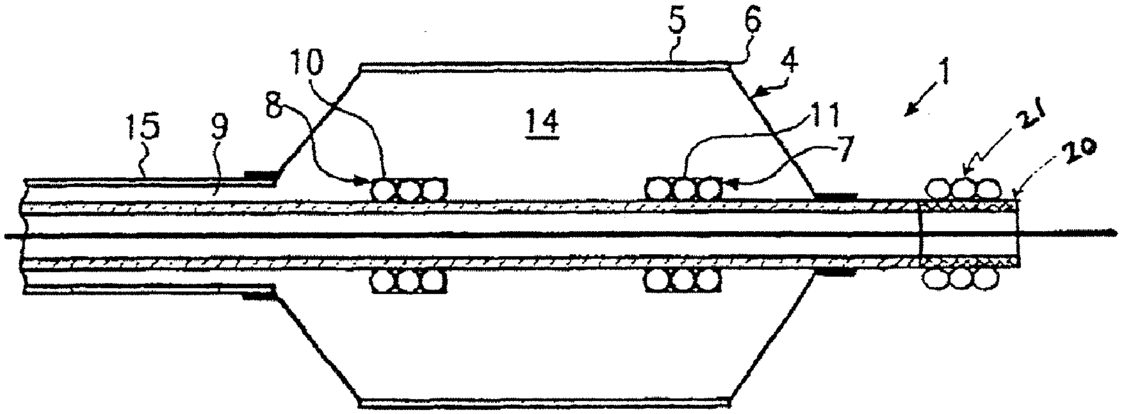
FIG. 7 is a schematically simplified view of the distal end of a catheter according to a further embodiment of the invention.

According to a further embodiment of the invention, and as schematically shown in FIG. 7, the elongate tubular member 2 includes a wire disposed along a length thereof in a spiral configuration 30. The spiral-configured wire 30 wrapped around at least a portion of a length of tube 2 improves the kink-resistance and push transfer capability of the catheter 1, especially when crossing tight lesions. Further, the wire includes at least a first marker section of radiopaque material 10 along a length of the tubular member. The first marker section can be disposed under the balloon 4, as depicted. However, if desired, the marker section can be disposed proximal or distal to the balloon member, as shown in FIG. 7. Referring to FIG. 7, at least one marker section is disposed along a tip of the catheter. Alternatively, the marker section can be disposed along the distal end section of the tubular member.

Figure 6:
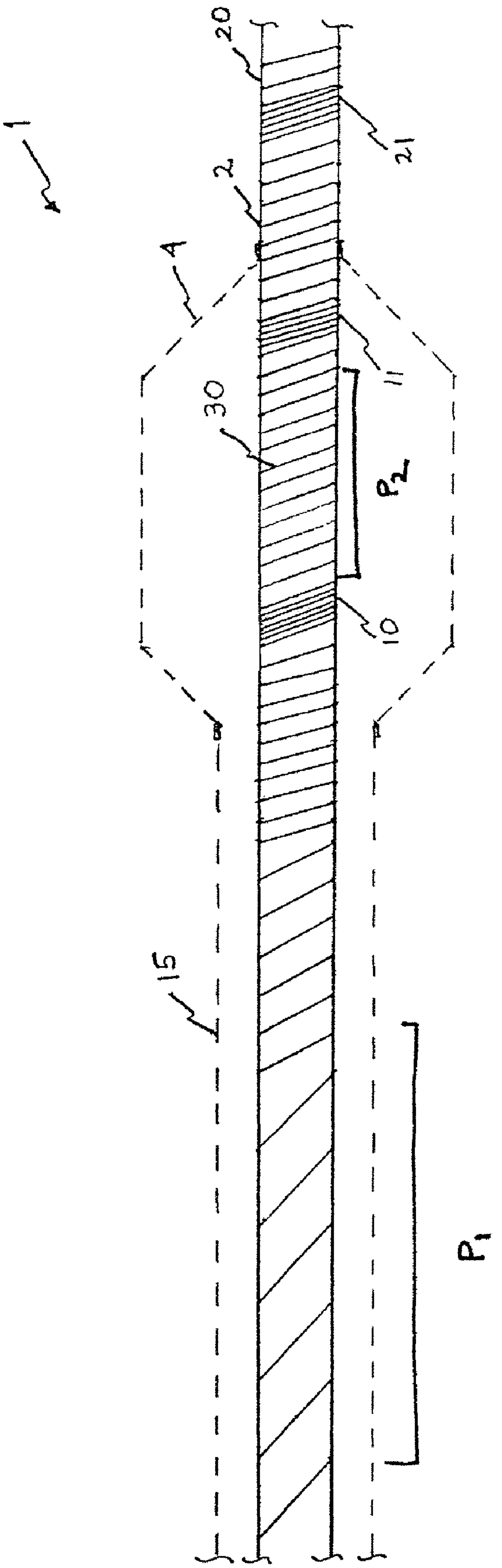
FIG. 6 is a cross sectional view of the distal end of a catheter having a marker at a tip thereof.

Referring back to FIG. 6, the wire can be formed, at least partially, from a radiopaque material. The wire can be disposed about the tubular member in varying slopes to define a pitch along a length of the spirally configured wire. For example, a stiffness gradient can be achieved along the length of the tubular member by shaping and configuring the wire to have a first pitch along a length thereof as shown as P1 and a second pitch along a second length of the tubular member as shown as P2 in FIG. 6. Accordingly, a tubular member having an increasing, decreasing or varied stiffness gradient can be achieved by incorporating a wire having a plurality of pitches along a length of the tubular member. In addition or alternatively, the wire can include a plurality of densities to achieve different attributes of stiffness along the length of the tubular member.

Further, the wire sections having greater wire density and tight or decreased wire spiral pitches along the tubular member 2 forms sections having greater visual contrasts under X-ray fluoroscopy thereby exhibits greater radiopacity. Also, greater pushability can be achieved.

For the purpose of illustration, the spirally configured wire 30 can be embedded into the tubular member 2 during the extrusion process or afterwards with an additional polymeric covering. The covering can be achieved in a variety of ways. For example, the covering can be formed from a coating sprayed or layered on the exterior surface of the wire. Alternatively, a tube can be formed and implemented to the tubular member.

It should be recognized that the tubular member of the invention can be utilized in a stent delivery device or other catheter body. Further, the catheter can be manufactured in a variety of ways including a coaxial catheter configuration or a side-by-side catheter configuration. The invention is not hereby limited.

In addition to the specific embodiments claimed below, the invention is also directed to other embodiments having any other possible combination of the dependent features claimed below and those disclosed above. As such, the particular features presented in the dependent claims and disclosed above can be combined with each other in other manners within the scope of the invention such that the invention should be recognized as also specifically directed to other embodiments having any other possible combinations. Thus, the foregoing description of specific embodiments of the invention has been presented for purposes of illustration and description. It is not intended to be exhaustive or to limit the invention to those embodiments disclosed.

Many modifications, variations, or other equivalents to the specific embodiments described above will be apparent to those familiar with the art. It is intended that the scope of this invention be defined by the claims below and those modifications, variations and equivalents apparent to practitioners familiar with this art.

What is claimed is:

1. A catheter comprising:

an elongate first tubular member having a proximal section, a distal section, and a lumen extending therethrough;

a balloon associated with the distal section of the first tubular member, the balloon having a proximal end and a distal end; and a wire disposed in at least the distal section of the first tubular member, the wire disposed in a spiral configuration and at least partially embedded in the tubular member, the wire including at least a first marker section of radiopaque material and a second marker section of radiopaque material, the first and second marker sections each formed of a varied density of the wire with the first marker section disposed proximate the proximal end of the balloon and the second marker section disposed proximate the distal end of the balloon.

2. The catheter of claim 1, wherein the first and second marker sections are disposed between the proximal and distal ends of the balloon.

3. The catheter of claim 1, wherein the first and second marker sections together extend from the proximal end to the distal end of the balloon.

4. The catheter of claim 1, wherein the wire includes plurality of densities along the length of the tubular member.

5. The catheter of claim 1, wherein the catheter further includes a cover over the wire.

6. The catheter of claim 5, wherein the cover is a coating.

7. The catheter of claim 5, wherein the cover is a tube.

8. The catheter of claim 1, wherein the wire has a circular cross-section.

9. The catheter of claim 1, wherein the wire has a flat, rectangular cross-section.

10. A catheter comprising:

an elongate first tubular member having a proximal section, a distal section, and a lumen extending therethrough;

a balloon associated with the distal section of the first tubular member, the balloon having a proximal end and a distal end; and a wire disposed in at least the distal section of the first tubular member in a spiral configuration and having at least a first marker section of radiopaque material and a second marker section of radiopaque material, the first and second marker sections each formed by an overlapping of the wire to form at least two layers of the wire.

11. The catheter of claim 10, wherein the radiopaque material is disposed between the proximal and distal ends of the balloon.

12. The catheter of claim 10, wherein the first marker section is disposed proximate the proximal end of the balloon and the second marker section is disposed proximate the distal end of the balloon.

13. The catheter of claim 10, wherein the first marker section of radiopaque material extends from the proximal end to the distal end of the balloon.

14. The catheter of claim 10, wherein the wire includes a plurality of densities along the length of the tubular member.

15. The catheter of claim 10, wherein the wire includes a plurality of pitches along the length of the tubular member.

16. The catheter of claim 15, wherein the first marker section includes a first spiral configuration having a first pitch proximal to the proximal end of the balloon and the second marker section includes a second pitch distal to the proximal end of the balloon.

17. The catheter of claim 16, wherein the second pitch is greater than the first pitch.

18. The catheter of claim 16, wherein the plurality of pitches defines a stiffness gradient along the length of the tubular member.

19. The catheter of claim 18 wherein the stiffness gradient decreases distally along the length of the tubular member.

20. The catheter of claim 10, wherein the catheter further includes a cover over the wire.

21. The catheter of claim 20, wherein the cover is a coating.

22. The catheter of claim 20, wherein the cover is a tube.

23. The catheter of claim 10, wherein the wire has a circular cross-section.

24. The catheter of claim 10, wherein the wire has a flat, rectangular cross-section.

25. The catheter of claim 10, wherein the wire is at least partially embedded in the tubular member.

26. The catheter of claim 1, wherein the wire is embedded in the tubular member.

27. The catheter of claim 1, wherein the wire includes a section of overlapping wire layers.

28. The catheter of claim 10, wherein the wire is embedded in the tubular member.

29. The catheter of claim 1, wherein the wire extends distal to the distal end of the balloon.

30. The catheter of claim 1, wherein the wire extends proximal to the proximal end of the balloon.

31. A catheter comprising:

an elongate first tubular member having a proximal section, a distal section, and a lumen extending therethrough;

a balloon associated with the distal section of the first tubular member, the balloon having a proximal end and a distal end; and a wire disposed in at least the distal section of the first tubular member, the wire disposed in a spiral configuration, the wire including at least a first marker section of radiopaque material and a second marker section of radiopaque material, the first and second marker sections each formed by a varied pitch of the wire.

32. The catheter of claim 31, wherein the wire includes a plurality of pitches along the length of the tubular member.

33. The catheter of claim 32, wherein the wire includes a first pitch proximal to the proximal end of the balloon and a second spiral configuration having a second pitch distal to the proximal end of the balloon.

34. The catheter of claim 33, wherein the second pitch is greater than the first pitch.

35. The catheter of claim 32, wherein the plurality of pitches define a stiffness gradient along the length of the tubular member.

36. The catheter of claim 35, wherein the stiffness gradient decreases distally along the length of the tubular member.

37. The catheter of claim 31, wherein the first and second marker sections are disposed between the proximal and distal ends of the balloon.

38. The catheter of claim 31, wherein the first and second marker sections together extend from the proximal end to the distal end of the balloon.

39. The catheter of claim 31, wherein the first marker section is disposed proximate the proximal end of the balloon and the second marker section is disposed proximate the distal end of the balloon.

40. The catheter of claim 31, wherein the wire includes a plurality of densities along the length of the tubular member.

41. The catheter of claim 31, wherein the catheter further includes a cover over the wire.

42. The catheter of claim 40, wherein the cover is a coating.

43. The catheter of claim 40, wherein the cover is a tube.

44. The catheter of claim 31, wherein the wire has a circular cross-section.

45. The catheter of claim 31, wherein the wire has a flat, rectangular cross-section.

46. The catheter of claim 31, wherein the wire is at least partially embedded in the tubular member.

47. The catheter of claim 31, wherein the wire includes a section of overlapping wire layers.

48. The catheter of claim 31, wherein the wire extends distal to the distal end of the balloon.

49. The catheter of claim 31, wherein the wire extends proximal to the proximal end of the balloon.

* * * * *